United States Patent [19]

Hoffman, Jr. et al.

[11] Patent Number: 4,483,023
[45] Date of Patent: Nov. 20, 1984

[54] HIGH-STRENGTH LIGAMENT PROSTHESIS

[75] Inventors: Harmon L. Hoffman, Jr., Wycoff; Steven Weinberg, Oakland, both of N.J.; John P. Park, Springdale, Ark.

[73] Assignee: Meadox Medicals, Inc., Oakland, N.J.

[21] Appl. No.: 295,160

[22] Filed: Aug. 21, 1981

[51] Int. Cl.³ ............................ A61F 1/04; A61F 5/04
[52] U.S. Cl. ............................................ 3/1; 128/92 C
[58] Field of Search ................ 3/1, 1.9, 1.4; 128/339, 128/92 C

[56] References Cited

U.S. PATENT DOCUMENTS

| | | | |
|---|---|---|---|
| 3,212,502 | 10/1965 | Myers | 128/339 |
| 3,805,300 | 4/1974 | Tascon-Alonso et al. | 3/1 |
| 3,877,570 | 4/1975 | Barry | 128/339 X |
| 3,882,551 | 5/1975 | Helmer et al. | 3/1 |
| 4,127,902 | 12/1978 | Homsy | 3/1 |
| 4,187,558 | 2/1980 | Dahlen et al. | 3/1 |
| 4,195,637 | 4/1980 | Gruntzig et al. | 3/1 |
| 4,209,859 | 7/1980 | Hoffman | 3/1 |
| 4,345,339 | 8/1982 | Muller et al. | 3/1 |

Primary Examiner—Richard J. Apley
Assistant Examiner—David J. Isabella
Attorney, Agent, or Firm—Blum, Kaplan, Friedman, Silberman & Beran

[57] ABSTRACT

A high-strength ligament prosthesis having biological acceptability, flexibility, porosity and resistance to prolonged stress in excess of 100 Kg with little change in modulus, and less than 20% ultimate elongation is provided. These characteristics make the high-strength prosthesis favorable for critical applications, such as knee and ankle repair. The high-strength prosthesis is constructed of a biological compatible yarn having an outer shell with an "H-beam" cross-section and a velour surface to encourage rapid invasion by host tissue and a reinforcing core of the same yarn. The ends of the reinforcing core and outer wall are fitted with end tips to limit displacement of the core within the outer shell and to facilitate positioning of the prosthesis during surgery with minimal effort. An enlarged elongated end tip is particularly well adapted for special surgical procedures, such as arthoscopic procedures.

13 Claims, 7 Drawing Figures

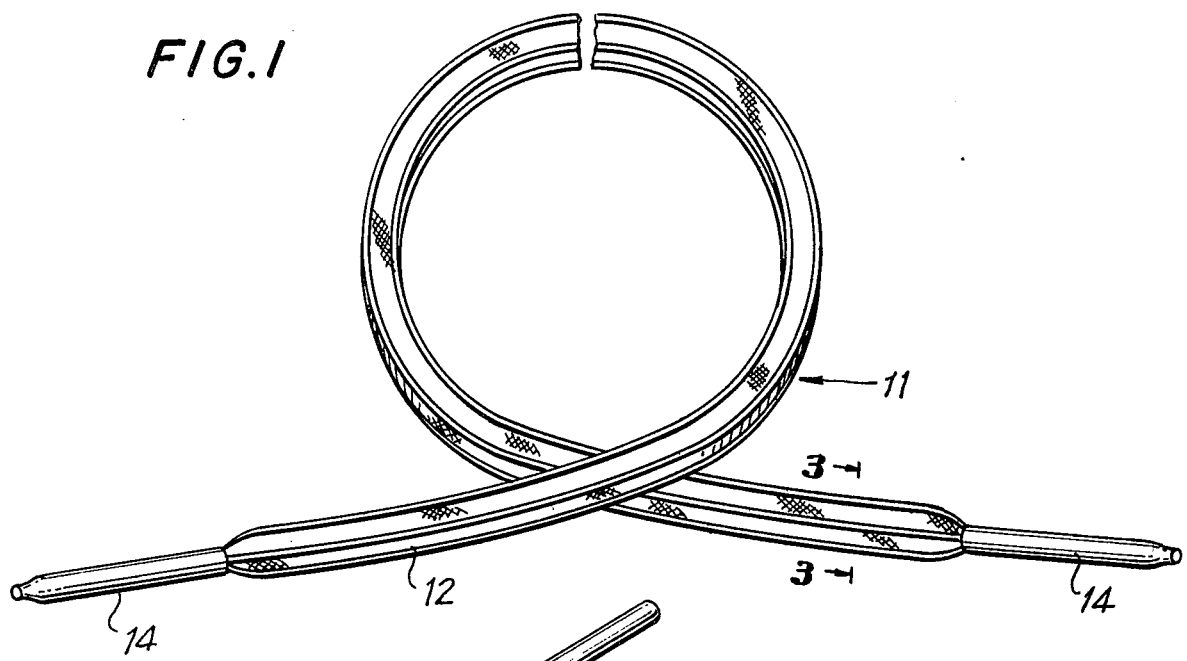
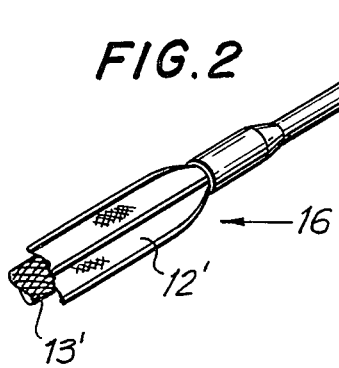
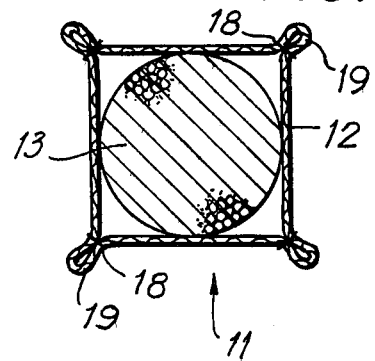
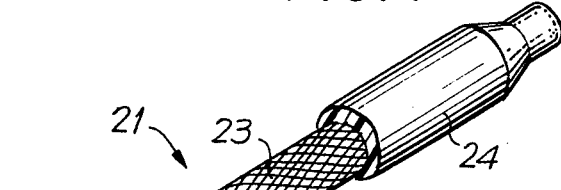
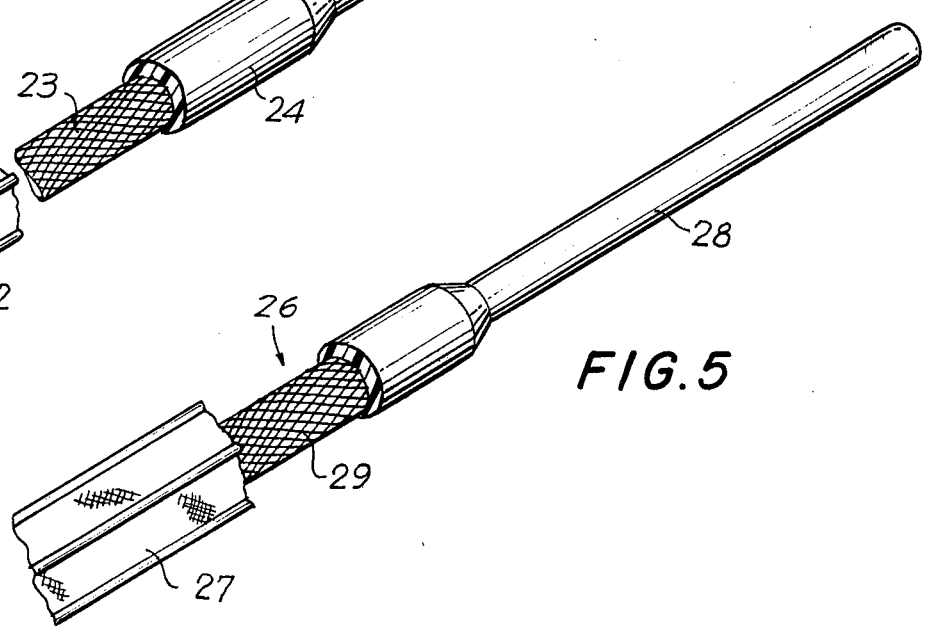

HIGH-STRENGTH LIGAMENT PROSTHESIS

BACKGROUND OF THE INVENTION

This invention relates generally to a ligament prosthesis, in particular to a high-strength ligament prosthesis.

The recognized need for and acceptance of artifical ligaments to replace or supplement natural ligaments is well known. In U.S. Pat. No. 4,209,859, issued on July 1, 1980, and assigned to the same assignee as this application, a ligament and tendon prosthesis of polyethylene terephthalate and a method of preparing same are described and claimed. The text of the previously issued patent is incorporated herein by reference.

The standard ligament prosthesis as described in the earlier patent is particularly well suited for surgical repair of shoulder injuries, such as an acromioclavicular dislocation. However, for surgical repair of ligaments subject to higher tensile loads, such as for surgical repair of the knee joint, a higher strength prosthesis is desirable.

SUMMARY OF THE INVENTION

Generally speaking, in accordance with the invention, a high-strength ligament prosthesis having greater tensile strength and lower stress elongation than standard ligament prostheses is provided. The high-strength prosthesis is formed of any biocompatible yarn material, preferably a Dacron material. To prepare a prothesis in accordance with the invention, a tubular fabric outer shell is heat-set, by a treatment at about 250° F. for about three minutes which provides rigidity and provides an open lumen for invasion by host tissue. The outer surface is preferably of a velour construction, but may also be of a woven, circularly-knit or warp-knit construction. The outer shell preferably has a "H-beam" cross-section and a reinforcing core formed of the same Dacron material. However, other cross sections would be acceptable.

The ends of the reinforceing core and ends of the outer shell of the prosthesis are capped by a heat-shrunk plastic material. The end tips serve to prevent displacement of the reinforcing core within the outer shell as well as providing surgical aids. The tips enable a surgeon to position the prosthesis with minimal effort. Generally, the tips extend for about one inch of length of the prosthesis. In accordance with a further embodiment of the invention, an extended tip of about six inches is provided for special surgical procedures, such as arthroscopic surgical procedures for repair of damaged knee ligaments in a procedure such as the MacIntosh repair procedure.

Accordinly, it is an object of the invention to provide an improved ligament prosthesis.

It is another object of the invention to provide a high-strength ligament prosthesis.

It is a further object of the invention to provide a high-strength ligament prosthesis having an outer shell and a reinforcing core.

Still another object of the invention is to provide an improved high-strength ligament prosthesis having end tips to aid in surgical placement of the prosthesis.

Still a further object of the invention is to provide an improved high-strength ligament prosthesis having extended end tips which is particularly well suited for use in arthroscopic surgical procedures.

Still other objects and advantages of the invention will in part be obvious and will in part be apparent from the specification.

The invention accordingly comprises an article of manufacture possessing the features, properties, and the relation of elements which will be exemplified in the article hereinafter described, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 is a perspective view of a high-strength ligament prosthesis constructed and arranged in accordance with the invention;

FIG. 2 is a partial perspective view of the end tip region of a high-strength ligament prosthesis having extended tips in accordance with another embodiment of the invention;

FIG. 3 is a cross-sectional view of the ligament prosthesis of FIG. 1, taken along lines 3—3 of FIG. 1;

FIG. 4 is an explode perspective view of the tip region of the ligament prosthesis of claim 1;

FIG. 5 is an exploded view of the tip region of the ligament prosthesis of FIG. 2;

DESCRIPTION OF THE PREFERRED EMBODIMENTS

Figure 6:
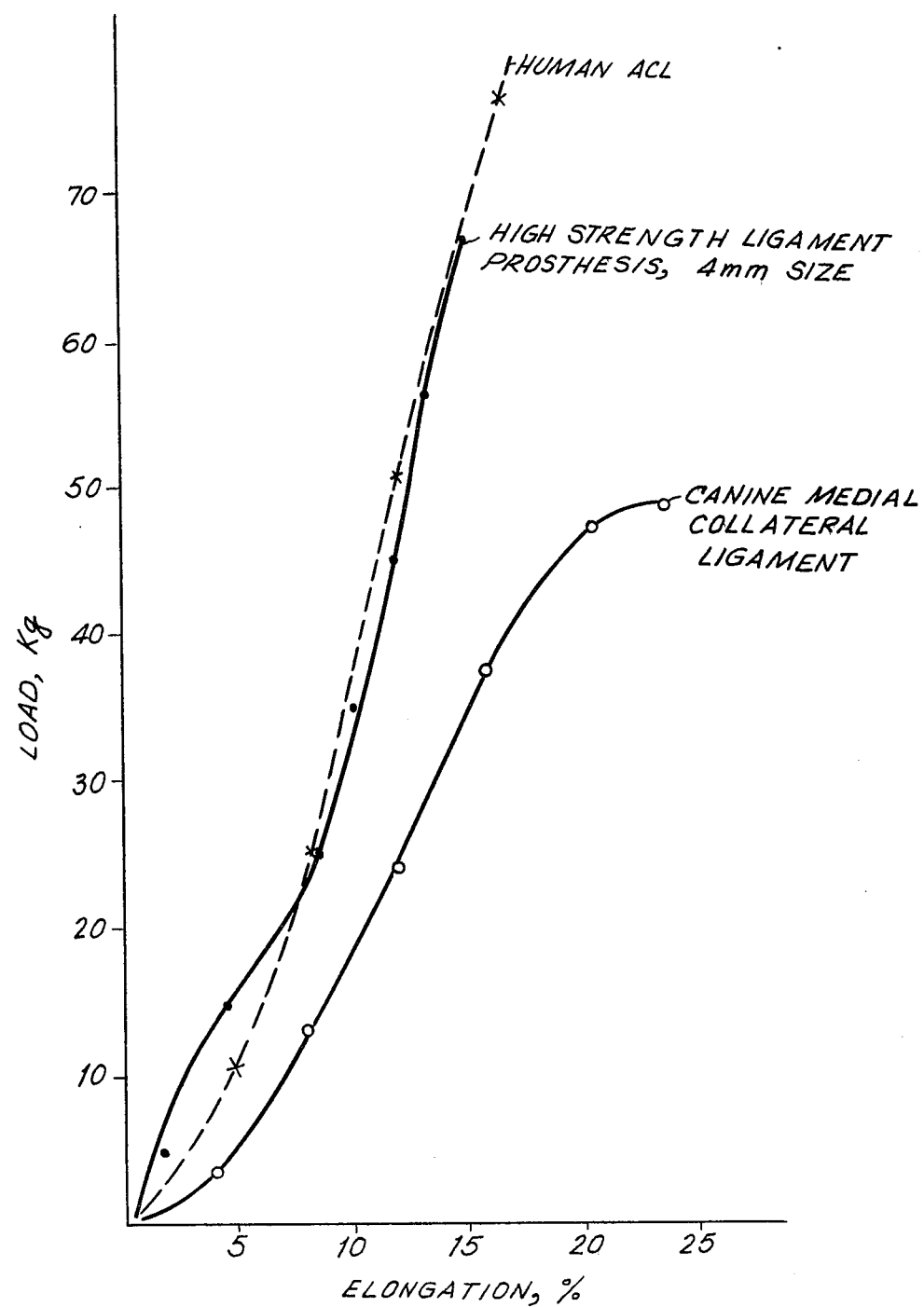
FIG. 6 is a graph indicating the tensile performance of a high-strength ligament prosthesis prepared in accordance with the invention after having been subject to continuous stress cycling.

The high-strength ligament prosthesis constructed and arranged in accordance with the invention represents an improvement of the standard artifical ligament replacement described and claimed in U.S. Pat. No. 4,209,859. The high-strength prosthesis is formed of any bio-compatible material, preferably a Dacron polyethylene terephthalate material which provides biological acceptability, flexibility, porosity and resistance to prolonged stress. The prosthesis has an outer wall or shell having a centrl reinforcing core. The outer shell may be prepared by weaving, circular-knitting or warp-knitting as shown in the earlier patent. The reinforcing core also may be woven, or it may be braided in form. In order to maintain position of the reinforcing core within the outer shell, the tips of the reinforcing core and the ends of the outer shell are secured by means of end tips or caps. Preferably, the end tips are plastic and serve to maintain the position and orientation of the core within the outer shell. Additionally, the end tips are substantially rigid tips, but sufficiently flexible to provide the surgeon with means to position the prosthesis during surgery. The plastic tips are preferably formed of a heat-shrinkable, biologically acceptable material, also a polyethylene terephthalate, polyvinylidene fluoride, or a polyolefin material.

Referring specifically to FIG. 1, a high-strength ligament prosthesis constructed and arranged in accordance with one embodiment of the invention is shown generally as 11. Prosthesis 11 includes an outer shell 12 having a desired length and thickness. The cross-section of outer shell 12 is selected as desired for providing various ultimate tensile strengths. The prosthesis may be from about 2.5 mm to 10 mm in outside diameter for providing various strengths as required. The cross-section may be circular, or preferably, have a "H-beam" cross-section as illustrated in FIG. 3. A reinforcing core 13 for providing the high-strength properties to ligament prosthesis 11 is shown in FIG. 3 cross-section. Prosthesis 11 also includes end tips 14 for securing the ends of outer shell 12 to the ends of reinforcing core 13 as illustrated in the exploded perspective view of FIG. 3 or to a reinforcing core 23 as illustrated in FIG. 4.

FIG. 2 illustrates a high-strength ligament prosthesis 16 constructed and arranged in accordance with another embodiment of the invention. Prosthesis 16 includes a similarly constructed and reinforcing core 13', but includes enlarged end tips 17. Enlarged end tips 17 secure the position of core 13' in outer shell 12' and are intended to assist in arthroscopic surgical procedures.

Referring specifically to the construction of the prosthesis in FIG. 3, outer shell 12 starts with a flattened tube having a diameter of between 30 and about 70 mm. The flattened tube is sewn together longitudinally along lines about 2 mm in from each edge using a Dacron thread 18 to form ridges 19. Outer shell 12 is then re-folded so that each of the original ridges now lie between two new folds and the new folds are simply sewn together longitudinally using additional Dacron threads. Outer shell 12, now having four ridges 19 is compacted by chemical treatment and is then heat-set in a mandrel as described in detail in U.S. Pat. No. 4,209,859.

During preparation, outer shell 12 is placed in a shrinking agent, such as $CH_2CL_2$, and $CH_2Cl_2$ in combination with $NO_2$. Conventionally, the material is simply exposed to the shrinking agent to effect the desired degree of compaction, the principal objective being to reduce the size of the openings between the threads, constituting the fabric. However, such fabrics subsequent to the shrinking operation, generally have a degree of extensibility greater than desired so that the fabric is compacted in the shrinking agent under restraint in the longitudinal direction which greatly reduces the extensibility of the compacted fabric. Generally, this enlongation at a given stress is reduced to at least about 50%.

Reinforcing core 13 is also formed of a biological compatible material; preferably, also a Dacron polyethylene terephthalate. The Dacron selected is a high-strength Dacron, commonly referred to as a high-tenacity fiber. Such fibers are generally used in the manufacture of automobile seat belts and tires. Reinforcing core 13 may be constructed in a woven form or a braid. The woven form of reinforcing core 13 is perferred, or a braided form may be used where more elongation is desired.

Referring now to FIG. 4, an exploded perspective view of the tip region of a high-strength ligament prosthesis 21 having an outer shell 22 and a pair of short-tips 24 is shown. Prosthesis 21 has an outer shell 22 and a reinforcing core 23 of about 75 mm in length, 6 mm in section and tips 24 are about 25 mm. Tips 24 cover the end region of outer shell 22 and secure it to the ends of reinforcing core 23. Tips 24 are formed of a heat-shrinkable polymeric material which is biologically acceptable, such as polypropolyne or polyethylene terephthalate. Tips 24 maintain the position of reinforcing core 23 within outer shell 22 and also provides assistance to the surgeon in positioning ligament prosthesis 21 during surgery.

In the exploded perspective in FIG. 5, the end of a ligament prosthesis 26 having an outer shell 27 and an elongated tip 28 is shown. Tip 28 secures the reinforcing core 29 to outer shell 27. In this embodiment of the invention, tip 28 engages the end portion of outer shell 27 and surrounds an extended portion of reinforcing cord 29 as shown in the perspective view of FIG. 5. The length of outer shell 27 is about 8 mm in section and 25 mm long and each tip 28 is approximately 15 mm in length making prosthesis 26 particularly useful for special types of surgical procedures, such as arthoscopic procedures.

A sample of a high-strength prosthesis constructed and arranged in accordance with the invention have been subjected to extensive mechanical testing. The results of measurements of critical tensile properties of the high-strength ligament prosthesis formed of Dacron polyethylene terephthalate having a 4 mm cross-section are shown in the following Table I:

TABLE I

| Material | Comparison of Material Properties | |
|---|---|---|
| | Maximum Stress, Megapascals | Ultimate Strength, Kilonewtons |
| Young Human ACL* | 37 ± 9.3 | 1.73 ± 0.66 |
| Meadox High Strength Dacron Prosthesis, 4 mm (Single) | 580 | 0.66 |
| Meadox High-Strength Dacron Prosthesis, 4 mm (double)** | (580) | 1.32 |
| Meadox High-Strength Dacron Prosthesis, 8 mm (single) | (580) | 2.16 |

*From the data described by Noyes and Grood (1).
**Simulating the ACL repair procedure by MacIntosh and Darby (3).

The data from Noyes and Grood (1) is taken from: Noyes, F. R., Grood, E. S., The Strength of the Anterior Cruciate Ligament in Human and Rhesus Monkeys, J. Bone Joint Surg., 58-A: 1074–1082, 1976.

The data for the canine medical collateral ligament is taken from the data of Ko and Cole (2): Ko, F. K., Cole, F. L., Development of Artificial Knee Ligaments, Part I, A Final Report for the Easter Seal Foundation. Philadelphia College of Textiles and Science, Philadelphia, PA, 1980.

The simulation of the ACL repair procedure by MacIntosh and Darby (3) is taken from: MacIntosh, D. L., Darby, T. A., Lateral Substitution Reconstruction (abstract), J. BoneJoint Surg., 58-B: 142, 1976.

Figure 7:
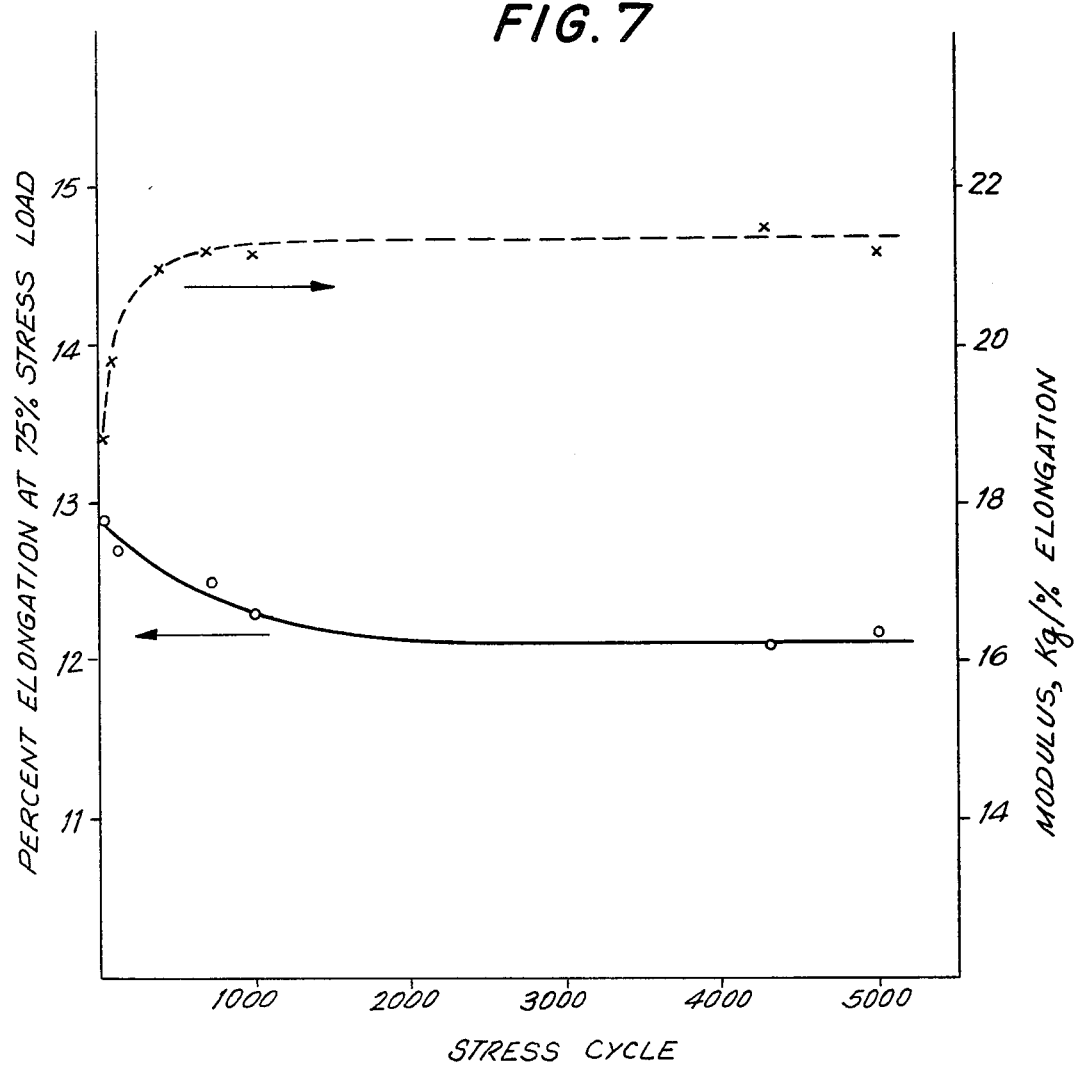
FIG. 7 is a graph illustrating the critical tensile properties of a high-strength ligament prosthesis constructed and arranged in accordance with the invention, the human ACL and a canine medial collateral ligament.

Stress/strain performance of the Dacron high-strength prosthesis in accordance with the invention has been compared for a human ACL (16–26 yrs) and a canine medial collateral ligament. The results of this comparison are illustrated in the graph of FIG. 7. In spite of differences in elongation rate, which are known to affect the results, the curve for the high-strength Dacron prosthesis is strikingly similar to those for the natural ligaments, particularly the human ACL. Additionally, the similarity in modulus value shown by the curves in FIG. 7 is considered to be a positive indication of the potential effectiveness of the high-strength Dacron prosthesis constructed in accordance with the invention.

The data in TABLE I indicate that the specific strength and maximum stress, MPa for the Dacron prosthesis exceeds that of the human ACL by a factor of about 20. This indicates that a high-strength prosthesis constructed and arranged in accordance with the invention having a smaller cross-section than the 4 mm tested will provide equivalent or greater strength in a ligament repair situation. The ultimate strength value listed for the 8 mm prosthesis is also greater than that of the human ACL.

Further tests were performed to illustrate that the high-strength ligament prosthesis constructed and arranged in accordance with the invention is particularly well suited for the intended uses. In this respect, representative samples of high-strength ligament prosthesis formed of Dacron polyethylene terephthalate were subjected to continuous stress cycling up to about 18,000 cycles. The cycling studies were carried out with an Instron tester, using high-density polyethylene fixtures to attach the Dacron prosthesis thereto. The prosthesis was placed through drill holes drilled in the plastic fixtures to form a loop fastened with a single square knot, imitating the configuration utilized in the MacIntosh repair procedure. The cycle period for the procedure was approximately 8 seconds. At the completion of stress cycling, the Dacron prosthesis was permitted to relax a few minutes and was then subjected to a normal tensile break cycle.

Although the stress cycle program including about 18,000 cycles represents only a small portion of the anticipated useful life of a ligament prosthesis, the results are indeed encouraging. Of particular significance is the small increase in elongation at 75% stress load— less than 1%—over the entire cycle program. The observed retention of elastic modulus suggests that the good elasticity should be retained indefinitely, barring mechanical damage to the prosthesis. Correspondingly, the modulus slope showed little change after the first 1,000 cycles. The ultimate breaking strength of the 4 mm ligament prosthesis after cycling was 132 Kg, indicating no loss as a result of the treatment. Results are illustrated in the graph of FIG. 6.

It will thus be seen that the objects set forth above, among those made apparent from the preceding description, are efficiently attained and since certain changes may be made in the above article without departing from the spirit and scope of the invention, it is intended that all matter contained in the above description and shown in the accompanying drawings shall be interpreted as illustrative and not in a limiting sense.

It is also to be understoon that the following claims are intended to cover all of the generic and specific features of the invention herein described, and all statements of the scope of the invention which, as a matter of language, might be said to fall therebetween.

What is claimed is:

1. A high-strength ligament prosthesis comprising an elongated polyethylene terephthalate fabric shell of reduced extensibility in the longitudinal direction and a central reinforcing core disposed within said outer shell, said fabric shell having a sufficiently open construction to permit ingrowth of body tissue to anchor the shell after implantation, and at least one end of the outer shell and reinforcing core having a deformable substantially rigid end tip secured thereon for coupling the outer shell and the end of said reinforcing core together to prevent displacement of the reinforcing core within the outer shell and for assisting in positioning the prosthesis during surgery.

2. The high-strength ligament prosthesis of claim 1, wherein said reinforcing core is formed of a polyethylene terephthalate material.

3. The high-strength ligament prosthesis of claim 2, wherein said polyethylene terephthalate is a high-tenacity fiber.

4. The high-strength ligament prosthesis of claim 2, wherein said reinforcing core is woven.

5. The high-strength ligament prosthesis of claim 2, wherein said reinforcing core is braided.

6. The high-strength ligament prosthesis of claim 3, wherein said outer shell has a H-beam appearance.

7. The high-strength ligament prosthesis of claim 3, wherein said outer shell has a velour surface.

8. The high-strength ligament prosthesis of claim 1, wherein said end tip is formed of a heat-shrinkable biologically compatible polymeric material.

9. The high-strength ligament prosthesis of claim 8, wherein said reinforcing core extends from the end of the outer shell a substantial distance and said end tip extends from the end region of said reinforcing core over the exposed length of said reinforcing core for assisting in positioning the prosthesis during surgery.

10. The high-strength ligament prosthesis of claim 1, wherein both ends of the outer shell and reinforcing core are coupled with substantially rigid end tips.

11. The high-strength ligament prosthesis of claim 4, wherein the woven reinforcing core is formed of a biologically acceptable high-tenacity fiber which permits ingrowth of body tissue.

12. A high-strength ligament prosthesis comprising an elongated polyethylene terephthalate fabric shell of reduced extensibility in the longitudinal direction and a central reinforceing core disposed within said outer shell, both said fabric shell and reinforcing core having a sufficiently open construction to permit ingrowth of body tissue to anchor the prosthesis in the joint, and at least one end of the outer shell and reinforcing core having a deformable substantially rigid end tip secured thereon for coupling the outer shell and the end of said reinforcing core together to prevent displacement of the reinforcing core within the outer shell and for assisting in positioning the prosthesis during surgery.

13. The high-strength ligament prosthesis of claim 12, wherein said end tip is formed of a heat-shrinkable biologically compatible polmeric material.

* * * * *